US00PP35304P2

(12) United States Plant Patent
Trees

(10) Patent No.: US PP35,304 P2
(45) Date of Patent: Aug. 8, 2023

(54) ***EUPHORBIA* PLANT NAMED 'BALEUPHFLUR'**

(50) Latin Name: *Euphorbia hypericifolia*
Varietal Denomination: Baleuphflur

(71) Applicant: Ball Horticultural Company, West Chicago, IL (US)

(72) Inventor: Scott C. Trees, Arroyo Grande, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 18/099,657

(22) Filed: Jan. 20, 2023

(51) Int. Cl.
*A01H 5/02* (2018.01)
*A01H 6/38* (2018.01)

(52) U.S. Cl.
USPC ..... Plt./302

(58) Field of Classification Search
USPC ..... Plt./302
CPC ..... A01H 5/02; A01H 5/00; A01H 6/38
See application file for complete search history.

(56) References Cited

U.S. PATENT DOCUMENTS

PP33,880 P2 * 1/2022 van Staalduinen .... A01H 6/385 Plt./304

* cited by examiner

*Primary Examiner* — June Hwu
(74) *Attorney, Agent, or Firm* — Audrey Charles

(57) ABSTRACT

A new and distinct cultivar of *Euphorbia* plant named 'Baleuphflur', characterized by its double-type, white-colored flowers, dark green-colored foliage often tinted dark red, and moderately vigorous, compact, mounded to spherical-like growth habit, is disclosed.

1 Drawing Sheet

Latin name of genus and species of plant claimed: *Euphorbia hypericifolia.*

Variety denomination: 'Baleuphflur'.

BACKGROUND OF THE INVENTION

The present invention relates to a new and distinct cultivar of *Euphorbia* plant botanically known as *Euphorbia hypericifolia* and hereinafter referred to by the cultivar name 'Baleuphflur'.

The new cultivar originated in a controlled breeding program in Guadalupe, Calif. during July 2017. The objective of the breeding program was the development of dark-leaved, compact, and well-branched *Euphorbia* having double flowers.

The new *Euphorbia* cultivar is the result of open-pollination. The female (seed) parent of the new cultivar is the proprietary *Euphorbia hypericifolia* breeding selection coded 21818-F, not patented, characterized by its double-type, white-colored flowers, dark green-colored foliage, and moderately vigorous, mounded growth habit. The male (pollen) parent of the new cultivar is the proprietary *Euphorbia hypericifolia* breeding selection coded 21815-A, not patented, characterized by its single-type, white-colored flowers, medium green-colored foliage, and moderately vigorous, mounded growth habit. The new cultivar was discovered and selected as a single flowering plant within the progeny of the above stated open-pollination during January 2018 in a controlled environment in Guadalupe, Calif.

Asexual reproduction of the new cultivar by terminal stem cuttings since January 2018 in Guadalupe, Calif. and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Baleuphflur' as a new and distinct cultivar of *Euphorbia* plant:

1. Double-type, white-colored flowers;
2. Dark green-colored foliage often tinted dark red; and
3. Moderately vigorous, compact, mounded to spherical-like growth habit.

Plants of the new cultivar differ from plants of the female parent primarily in having a more compact growth habit. Plants of the new cultivar differ from plants of the male parent primarily in having double-type flowers and a more compact growth habit.

Of the many commercially available *Euphorbia* cultivars, the most similar in comparison to the new cultivar is Euphoric Double White '16EUPD1', U.S. Plant Pat. No. 33,880. However, in comparison, plants of the new cultivar differ from plants of '16EUPD1' in at least the following characteristics:

1. Plants of the new cultivar have fewer cyathia per cyme than plants of '16EUPD1'; and
2. Plants of the new cultivar have a shade of yellow-green stem color that is different from plants of '16EUPD1'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Baleuphflur'. The plants were approximately 5-months old and were grown in twelve inch hanging baskets at three plants per basket. Plants were given three pinches prior to transplant.

DETAILED BOTANICAL DESCRIPTION

Figure 1:
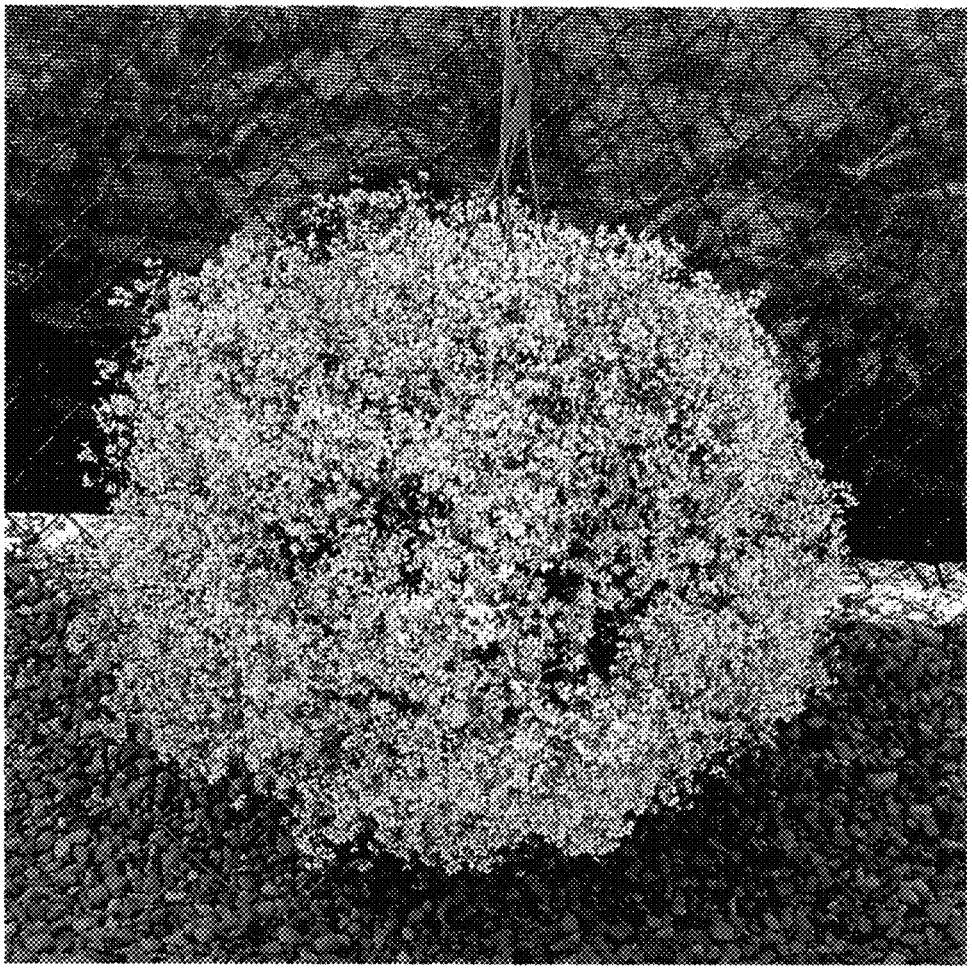
FIG. 1 illustrates a side view of the overall growth of 'Baleuphflur'.
Figure 2:
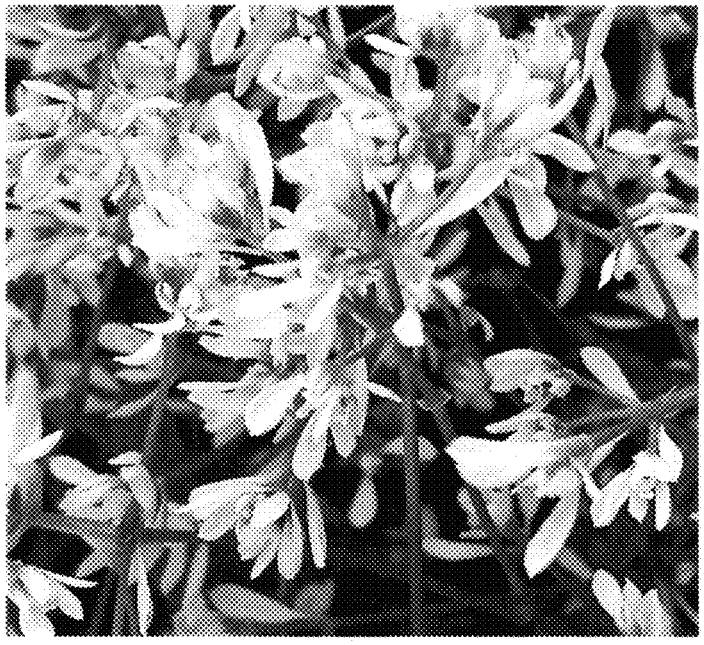
FIG. 2 illustrates a close-up view of the inflorescences of 'Baleuphflur'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in August 2022 under natural light conditions in Naperville, Ill.

The following descriptions and measurements describe approximately 5-month-old plants produced from cuttings from stock plants and grown under conditions comparable to those used in commercial practice. The plants were grown in in twelve inch hanging baskets at three plants per basket for approximately 12 weeks in an outdoor nursery in West Chicago, Ill. Plants were given three pinches prior to transplant. Prior to transplant plants were grown in a polycarbonate greenhouse in West Chicago, Ill. Greenhouse temperatures were maintained at approximately 75° F. to 80° F. (24° C. to 27° C.) during the day and approximately 65° F. to 70° F. (18° C. to 21° C.) during the night. Supplemental lighting was used for first two weeks after sticking. Measurements and numerical values represent averages of typical plants.

Botanical classification: *Euphorbia hypericifolia* 'Baleuphflur'.

Parentage:

*Female parent*.—Proprietary *Euphorbia hypericifolia* breeding selection coded 21818-F, not patented.

*Male parent*.—Proprietary *Euphorbia hypericifolia* breeding selection coded 21815-A, not patented.

Propagation:

*Type cutting*.—Terminal stem.

*Time to initiate roots*.—Approximately 7 to 10 days.

*Time to produce a rooted cutting*.—Approximately 3 to 4 weeks.

*Root description*.—Fine, fibrous.

*Rooting habit*.—Freely branching.

Plant description:

*Commercial crop time*.—Approximately 5 to 7 weeks from a rooted cutting to finish in a 10 cm container.

*Growth habit and general appearance*.—Moderately vigorous, compact, mounded to spherical-like growth habit.

*Size*.—Height from soil level to top of plant plane: Approximately 38.0 cm. Height from lowest point to top of plant plane: Approximately 60.0 cm. Width: Approximately 68.0 cm.

*Branching habit*.—Freely branching, divergent, pinching enhances branching. Quantity of branches per plant: Approximately 6 main basal branches and 14 main lateral branches.

*Lateral branch*.—Shape: Round in cross section. Strength: Strong, flexible. Length to base of inflorescence: Approximately 19.0 cm. Diameter: Approximately 4.0 mm. Length of central internode: Approximately 3.5 cm. Texture: Glabrous. Color of young and mature stems: 146D with 187A at nodes.

Foliage description:

*General description*.—Quantity of leaves per branch: Approximately 4 to 6. Fragrance: None detected. Form: Simple. Arrangement: Opposite.

*Leaves*.—Aspect: Primarily perpendicular to stem. Shape: Elliptic to narrowly elliptic. Margin: Entire, ciliate. Apex: Broadly acute. Base: Rounded to broadly attenuate. Venation pattern: Pinnate. Length of mature leaf: Approximately 2.6 cm. Width of mature leaf: Approximately 1.6 cm. Texture of upper and lower surfaces: Sparsely pubescent. Color of upper surface of young and mature foliage: 137A to 137B often tinted with 187A with venation indistinguishable from lamina. Color of lower surface of young and mature foliage: Closest to 138B with venation indistinguishable from lamina.

*Petiole*.—Length: Approximately 1.0 cm to 2.0 cm. Diameter: Approximately 1.0 mm. Texture: Sparsely pubescent. Color: 146C.

Flowering description:

*Flowering habit*.—'Baleuphflur' is freely flowering under outdoor growing conditions with substantially continuous blooming from late spring through autumn and year-round in greenhouse environment.

*Lastingness of individual cyanthium*.—Approximately 20 to 30 days.

Inflorescence description:

*General description*.—Type: Cyathia arranged in terminal and axillary cymes, terminal cymes having 3 to 4 axes. Aspect: Primarily facing upward and outward. Quantity of inflorescences per plant: Approximately 20 terminal compound cymes and approximately 10 axillary compound cymes per branch with approximately 6 cymes per each compound cyme. Fragrance: None detected. Depth or height of cyme: Approximately 1.4 cm. Width: Approximately 1.7 cm.

*Rachis*.—Strength: Strong. Aspect: Acute angle to stem. Length: Approximately 2.0 cm to 3.5 cm. Diameter: Approximately 1.0 mm. Texture: Glabrous. Color: 146B with 187A at axis.

Flower description:

*Bud just before opening*.—Shape: Obovoid. Length: Approximately 3.0 mm. Diameter: Approximately 2.0 mm. Texture: Glabrous. Color: NN155D.

*Cyathia*.—Quantity per cyme: 3 to 4. Appearance: Cyathium, asepalous and apetalous, comprised of an involucre that surround the female flower, and male flowers; 4 petaloid nectaries at the upper rim. Fragrance: Not detected. Depth: Approximately 5.0 mm. Width: Approximately 8.0 mm.

*Involucre*.—Length: Approximately 3.0 mm. Width: Approximately 2.0 mm. Texture: Glabrous. Color: 144A. Length of petaloid nectaries: Approximately 1.5 mm. Width of petaloid nectaries: Approximately 1.0 mm. Texture of upper and lower surfaces of petaloid nectaries: Glabrous. Color of petaloid nectaries: NN155A with base of 144A.

*Flower bracts*.—Quantity: 6 to 10 per cyathium. Arrangement: In multiple whorls with lowest two opposite. Shape: Obovate. Margin: Entire. Apex: Mucronate to rounded. Base: Attenuate. Length: Approximately 4.0 mm to 6.0 mm. Width: Approximately 1.0 mm to 2.0 mm. Texture of upper and lower surfaces: Glabrous. Color of upper surface: NN155A. Color of lower surface: NN155A with 144A at base.

*Cyathia pedicel*.—Length: Approximately 0.5 mm to 0.8 mm. Diameter: Less than 1.0 mm. Texture: Glabrous. Color: 144A.

*Reproductive organs*.—Androecium: Stamen quantity: 2 to 6. Length: Approximately 1.0 mm to 2.0 mm. Anther shape: Oval. Anther color: 158C. Pollen amount: Sparse. Pollen color: 158D. Gynoecium: Pistil quantity: 1 per cyathium, ovary supported on a pedicel of approximately 1.0 mm in length and color of 144A, 3 styles each 2-cleft, 6 stigmas. Pistil length (not including pedicel): Approximately 2.0 mm. Stigma shape: Rounded. Stigma length: Less than 1.0 mm. Stigma color: NN155D, transparent. Style length: Approximately 1.0 mm. Style color: NN155D, transparent. Ovary diameter: Approximately 1.0 mm. Ovary color: 144A.

Seed and fruit production: Neither seed nor fruit production has been observed.

Disease and pest resistance: Resistance to pathogens and pests common to *Euphorbia* has not been observed.

What is claimed is:

1. A new and distinct cultivar of *Euphorbia* plant named 'Baleuphflur', substantially as herein illustrated and described.

* * * * *